United States Patent [19]

Bourzat et al.

[11] Patent Number: 5,608,102

[45] Date of Patent: Mar. 4, 1997

[54] PROCESS FOR THE PREPARATION OF β-PHENYLISOSERINE AND ITS ANALOGUES

[75] Inventors: Jean-Dominique Bourzat, Vincennes; Alain Commerçon, Vitry-Sur-Seine, both of France

[73] Assignee: Rhone-Poulenc Rorer S.A., Antony, France

[21] Appl. No.: 295,677

[22] PCT Filed: Mar. 8, 1993

[86] PCT No.: PCT/FR93/00224

§ 371 Date: Sep. 26, 1994

§ 102(e) Date: Sep. 26, 1994

[87] PCT Pub. No.: WO93/17997

PCT Pub. Date: Sep. 16, 1993

[30] Foreign Application Priority Data

Mar. 10, 1992 [FR] France .................... 92 02821

[51] Int. Cl.$^6$ .............. C07C 229/34; C07D 205/02
[52] U.S. Cl. ................. 560/39; 548/952; 560/28; 560/29; 562/444
[58] Field of Search ............. 548/952; 560/39, 560/28, 29; 562/444

[56] References Cited

U.S. PATENT DOCUMENTS

| 4,924,012 | 5/1990 | Colin et al. | 549/510 |
| 5,041,643 | 8/1991 | Tinti et al. | 562/561 |
| 5,175,315 | 12/1992 | Holton | 549/510 |
| 5,294,737 | 3/1994 | Ojima | 562/444 |
| 5,304,670 | 4/1994 | Correa et al. | 560/39 |

FOREIGN PATENT DOCUMENTS

| 0402322 | 12/1990 | European Pat. Off. |
| 0400971 | 12/1990 | European Pat. Off. |

OTHER PUBLICATIONS

I. Ojima et al., "Azetidines and Bisazetidines. Their Synthesis and Use as the Key Intermediates to Enantiomerically Pure Diamines, Amino Alcohols, and Polyamines". Journal of Organic Chemistry vol. 56, No. 18 (1991) pp. 5263–5277.
Tetrahedron Letters, vol. 31, No. 44, 1990, pp. 6429–6432; C. Palomo et al. "Highly Stereoselective Synthesis of alpha–hydroxy beta–amino acids through beta–lactams: application to the Synethesis of the Taxol and Bestatin Side Chains and Related Systems".

*Primary Examiner*—Gary Geist
*Assistant Examiner*—Barbara S. Frazier
*Attorney, Agent, or Firm*—Finnegan, Henderson, Farabow, Garrett & Dunner, L.L.P.

[57] ABSTRACT

This invention relates to a method for preparing β-phenylisoserine and analogues thereof having general formula (I)

$$H_2N\cdots \underset{Ar}{\overset{S\phantom{xx}R'''}{\diagdown\phantom{xx}\diagup}}\underset{OH}{\overset{COOR}{\diagup}} \quad (I)$$

from an aromatic aldehyde and an α-methylarylamine-S, and through a lactam of general formula (II) as described herein. The acids of general formula (I) (R=H) may be used to prepare taxane derivatives having remarkable antitumoral and antileukaemic activity.

10 Claims, No Drawings

PROCESS FOR THE PREPARATION OF β-PHENYLISOSERINE AND ITS ANALOGUES

DESCRIPTION OF THE INVENTION

This application is a 371 PCT/FR93/0024, filed Mar. 8, 1993.

The present invention relates to new process for the preparation of β-phenylisoserine and its analogues of general formula:

which are particularly useful for preparing taxane derivatives which have remarkable antitumor and antileukaemic activities.

In the general formula (I), Ar represents an aryl radical and R represents a hydrogen atom or an alkyl radical containing 1 to 4 carbon atoms, which is optionally substituted by a phenyl radical, or a phenyl radical.

Preferably, Ar represents a phenyl or an α- or β-naphthyl radical which is optionally substituted by one or more atoms or radicals chosen from halogen atoms (fluorine, chlorine, bromine, iodine) and alkyl, aryl, aralkyl, alkoxy, alkylthio, aryloxy, arylthio, hydroxy, hydroxyalkyl, mercapto, formyl, acylamino, aroylamino, alkoxycarbonylamino, amino, alkylamino, dialkylamino, carboxy, alkoxycarbonyl, carbamoyl, dialkylcarbamoyl, cyano, nitro and trifluoromethyl radicals, it being understood that the alkyl radicals and the alkyl portions of the other radicals contain 1 to 4 carbon atoms and that the aryl radicals are phenyl or α- or β-naphthyl radicals.

More particularly, Ar represents a phenyl radical which is optionally substituted by one or more atoms or radicals, which are identical or different, chosen from halogen atoms and alkyl, alkoxy, amino, alkylamino, dialkylamino, acylamino, alkoxycarbonylamino and trifluoromethyl radicals.

Still more particularly, Ar represents a phenyl radical which is optionally substituted by a chlorine or fluorine atom or by an alkyl (methyl), alkoxy (methoxy), dialkylamino (dimethylamino) or acylamino (acetylamino) radical.

It is known to prepare β-phenylisoserine by hydrolysis of a lactam under the conditions described by C. Palomo et al., Tetrahedron Letters, 31, 6429–6439 (1990).

Threo-β-phenylisoserine can be obtained by the action of ammonia on a cis-β-phenylglycidic acid ester followed by the action of baryta, so as to avoid racemization on the β-phenylisoserine amide obtained as an intermediate under the conditions described by E. Kamandi et al., Arch. Pharmaj., 307 871–878 (1974).

The β-phenylisoserine can also be obtained under the conditions described in International Application PCT WO-A-91/13053 by passing via N-benzyl-β-phenylisoserine. portion contains 1 to 4 carbon atoms or nitro radicals. More particularly, Ph represents a phenyl radical which is optionally substituted by one or more radicals, which are identical or different, chosen from methoxy, methylthio, methylamino, dimethylamino or nitro radicals.

Generally, the hydrogenolysis is performed by means of hydrogen in the presence of a catalyst.

More particularly, a palladium on carbon containing 1 to 10% by weight of palladium or palladium dihydroxide on carbon containing up to 10% by weight of palladium are used as catalyst.

The hydrogenolysis is performed in an organic solvent or a mixture of organic solvents.

It is particularly advantageous to carry out the procedure in acetic acid optionally combined with an aliphatic alcohol containing 1 to 4 carbon atoms. A mixture of acetic acid and methanol is of a very special interest.

According to a preferred embodiment of the process, the procedure is carried out under a hydrogen pressure which may be between 1 and 50 bars.

The temperature for carrying out the process is generally between 20° and 80° C. and preferably between 50° and 70° C.

The hydrogen required for the hydrogenolysis may also be provided by a compound which releases hydrogen by chemical reaction or by thermal decomposition such as ammonium formate.

The product of general formula (II) may be obtained by hydrolysis or alcoholysis of a product of general formula:

in which Ar and Ph are defined as above.

It is particularly advantageous to carry out an alcoholysis by means of an alcohol of general formula R—OH in which R is defined as above, the procedure being carried out in an acidic medium.

Preferably, the alcoholysis is performed by means of methanol in the presence of a strong inorganic acid such as hydrochloric acid.

It is advantageous to perform the alcoholysis at a temperature close to the reflux temperature of the reaction medium.

The product of general formula (III) may be obtained by saponification or hydrogenolysis of a product of general formula:

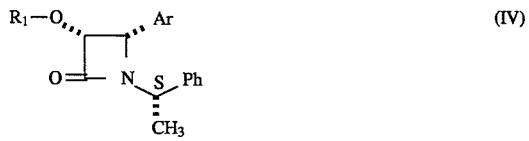

in which Ar and Ph are defined as above and $R_1$ represents a group protecting the alcohol functional group in the form of an ester or an ether, followed by separation of the (3R,4S) diastereoisomer of general formula (III) from the other diastereoisomers.

More particularly, $R_1$ represents an alkyl, phenylalkyl or phenyl radical or a $R'_1$—CO radical in which $R'_1$ represents an alkyl, phenylalkyl or phenyl radical.

Generally, when the alcohol functional group is protected in the form of an ester, a saponification is performed by means of an inorganic or organic base such as ammonium hydroxide, lithium hydroxide, sodium hydroxide or potassium hydroxide, in a suitable solvent.

An aqueous-organic medium such as a methanol-water or a tetrahydrofuran-water mixture is preferably used as solvent. The reaction is carried out at a temperature of between −10° and +20° C.

Generally, when the alcohol functional group is protected in the form of an ether, a hydrogenolysis is performed by means of hydrogen, optionally generated in situ, for example, by decomposition of ammonium formate, in the presence of a catalyst such as palladium black containing 1 to 10% palladium (w/w).

The separation of the (3R,4S) diastereoisomer may be performed by selective crystallization from a suitable organic solvent such as ethyl acetate, optionally in the presence of an aliphatic hydrocarbon such as hexane or by chromatography on silica.

The product of general formula (IV) may be obtained by cycloaddition of an imine of general formula:

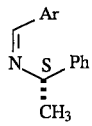
(V)

in which Ar and Ph are defined as above, onto an acid halide of general formula:

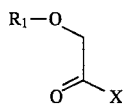
(VI)

in which $R_1$ is defined as above and X represents a halogen atom such as a bromine or chlorine atom.

Generally, the reaction is carried out at a temperature of between −20° and 50° C., preferably in the vicinity of 0° C., in the presence of a base chosen from tertiary amines (triethylamine, N-methyl-morpholine) or pyridine, in an organic solvent chosen from optionally halogenated aliphatic hydrocarbons such as methylene chloride or chloroform and aromatic hydrocarbons such as benzene, toluene or xylenes.

The product of general formula (V) may be obtained under the conditions described by M. Furukawa et al., Chem. Pharm. Bull., 25 (1), 181–184 (1977).

The product of general formula (I), in which R represents a hydrogen atom, may also be obtained by saponification of a product of general formula (I), in which R represents an alkyl radical containing 1 to 4 carbon atoms, which is optionally substituted by a phenyl radical, or a phenyl radical.

Generally, the saponification is performed by means of an inorganic base such as an alkali metal hydroxide (lithium hydroxide, sodium hydroxide), an alkali metal carbonate or bicarbonate (sodium bicarbonate, potassium carbonate) in an aqueous-alcoholic medium such as a methanol-water mixture, the procedure being carried out at a temperature of between 10° and 40° C., preferably close to 25° C.

The acids of general formula (I) are particularly useful for preparing the taxane derivatives of general formula:

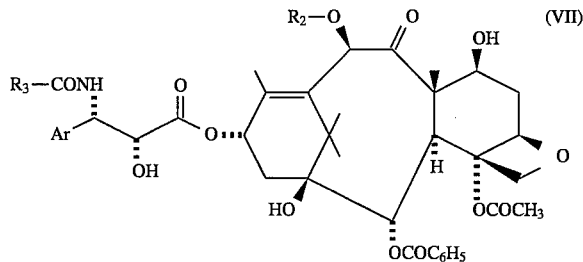
(VII)

in which Ar is defined as above, $R_2$ represents a hydrogen atom or an acetyl radical and $R_3$ represents a phenyl radical which is optionally substituted by one or more atoms or radicals, which are identical or different, chosen from halogen atoms and alkyl, hydroxyl, alkoxy, alkanoyl, alkanoyloxy, nitro, amino, alkylamino, dialkylamino, carbamoyl or trifluoromethyl radicals, the alkyl radicals and the alkyl portions of the other radicals containing 1 to 4 carbon atoms, or alternatively $R_3$ represents a radical $R_4$—O— in which $R_4$ represents:

a straight or branched alkyl radical containing 1 to 8 carbon atoms, an alkenyl radical containing 3 to 6 carbon atoms, a cycloalkyl radical containing 3 to 6 carbon atoms, a cycloalkenyl radical containing 4 to 6 carbon atoms, these radicals being optionally substituted by one or more substituents chosen from halogen atoms and hydroxyl radicals, alkyloxy radicals containing 1 to 4 carbon atoms, dialkylamino radicals in which each alkyl portion contains 1 to 4 carbon atoms, piperidino radicals, morpholino radicals, 1-piperazinyl radicals (optionally substituted in −4 by an alkyl radical containing 1 to 4 carbon atoms or by a phenylalkyl radical whose alkyl portion contains 1 to 4 carbon atoms), cycloalkyl radicals containing 4 to 6 carbon atoms, alkenyl radicals containing 4 to 6 carbon atoms, phenyl radicals, cyano radicals, carboxy radicals or alkyloxycarbonyl radicals whose alkyl portion contains 1 to 4 carbon atoms, or a phenyl radical which is optionally substituted by one or more atoms or radicals chosen from halogen atoms and alkyl radicals containing 1 to 4 carbon atoms or alkyloxy radicals containing 1 to 4 carbon atoms, or a saturated or unsaturated nitrogen-containing heterocyclyl radical containing 5 or 6 members and optionally substituted by one or more alkyl radicals containing 1 to 4 carbon atoms, which possess remarkable antitumor and antileucemic properties.

The product of general formula (VII) in which Ar represents a phenyl radical, $R_2$ represents an acetyl radical and $R_3$ represents a phenyl radical is known by the name of taxol and that for which Ar represents a phenyl radical, $R_2$ represents a hydrogen atom and $R_3$ represents a tert-butoxy radical is known by the name of Taxotere.

The taxane derivatives of general formula (VII) may be obtained by the action of an acid of general formula:

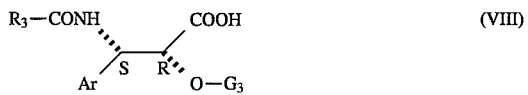
(VIII)

an which Ar and $R_3$ are defined as above and $G_3$ represents a group which protects the hydroxide functional group such as a methoxymethyl, (1-ethoxy) ethyl, benzyloxymethyl, (β-trimethylsilylethoxy)methyl, tetrahydropyranyl, 2,2,2-trichloroethoxymethyl or 2,2,2-trichloroethoxycarbonyl radical optionally in the form of a halide, an anhydride or a mixed anhydride, on a taxane derivative of general formula:

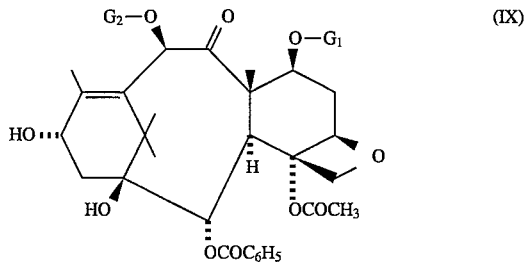
(IX)

in which $G_1$ represents a group which protects the hydroxyl functional group such as 2,2,2-trichloroethoxycarbonyl or trialkylsilyl, dialkylarylsilyl, alkyldiarylsilyl or triarylsilyl radical in which each alkyl portion contains 1 to 4 carbon atoms and each aryl portion preferably represents a phenyl radical and $G_2$ represents an acetyl radical or a group which protects the hydroxyl functional group such as a 2,2,2-trichloroethoxycarbonyl radical, to give a product of general formula:

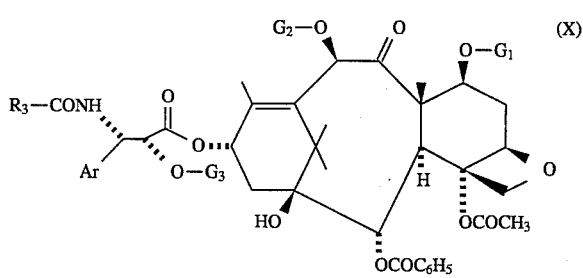

(X)

in which Ar, $R_3$, $G_1$, $G_2$ and $G_3$ are defined as above, followed by the replacement of the groups $G_1$, $G_2$ and $G_3$ by hydrogen atoms.

Generally, the esterification is performed in the presence of a condensing agent such as a carbodiimide such as dicyclohexylcarbodiimide or a reactive carbonate such as 2-pyridyl carbonate and an activating agent such as an aminopyridine such as 4-dimethylaminopyridine or 4-pyrrolidinopyridine, the procedure being carried out in an organic solvent such as an aromatic hydrocarbon (benzene, toluene, xylene, ethylbenzene, isopropylbenzene, chlorobenzene), an ether (tetrahydrofuran), a nitrile (acetonitrile) or an ester (ethyl acetate), at a temperature of between 0° and 90° C.

The replacement of the protecting groups $G_1$, $G_2$ and $G_3$ with hydrogen atoms is generally performed by treating with zinc in the presence of acetic acid at a temperature of between 30° and 60° C. or by means of an inorganic or organic acid such as hydrochloric acid or acetic acid in solution in an aliphatic alcohol containing 1 to 3 carbon atoms in the presence of zinc when one of the protecting groups represents a 2,2,2-trichloroethoxycarbonyl radical or by treating in acidic medium when one of the protecting groups represents a silylated radical.

The acid of general formula (VIII) may be obtained by saponification of an ester of general formula

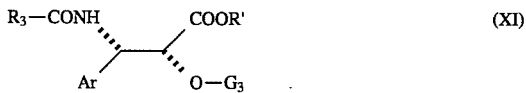

(XI)

in which Ar, $R_3$ and $G_3$ are defined as above and R' represents an alkyl radical containing 1 to 4 carbon atoms, which is optionally substituted by a phenyl radical, or a phenyl radical, by means of an inorganic base such as an alkali metal hydroxide (lithium hydroxide, sodium hydroxide), an alkali metal carbonate or bicarbonate (sodium bicarbonate, potassium carbonate) in an aqueous-alcoholic medium such as a methanol-water mixture, the procedure being carried out at a temperature of between 10° and 40° C., preferably close to 25° C.

The product of general formula (XI) may be obtained under the usual conditions for the preparation of ethers, and more particularly according to the processes described by J-N. Denis et al., J. Org. Chem., 51, 46–50 (1986) from the product of general formula:

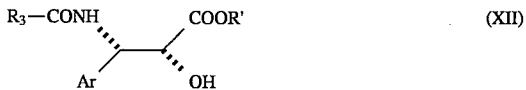

(XII)

in which Ar, $R_3$ and R' are defined as above.

The product of general formula (XII) may be obtained by the action of a benzoyl halide whose phenyl nucleus may be optionally substituted or by the action of a product of general formula:

$R_4$—O—CO—X (XIII)

in which $R_4$ is defined as above and X represents a halogen atom (fluorine, chlorine) or a residue —O—$R_4$ or —O—CO—O$R_4$, on a product of general formula (I) in which R represents an alkyl radical containing 1 to 4 carbon atoms, which is optionally substituted by a phenyl radical, or a phenyl radical.

Generally, the procedure is carried out in an organic solvent such as methylene chloride in the presence of an inorganic base such as sodium bicarbonate.

The product of general formula (XII) in which Ar represents a phenyl radical substituted by a cyano radical may be obtained by dehydration of a product of general formula (XII) in which Ar represents a phenyl radical substituted by a carbamoyl radical and the alcohol functional group is preferably protected by a silylated radical, followed by the replacement of the protecting group by a hydrogen atom.

The dehydration may be generally performed according to the usual methods for the preparation of nitriles from amides. For example, phosphorus oxychloride in pyridine is used.

The taxane derivatives of general formula (VII) may also be obtained by first converting the product of general formula (XII) to an oxazolidine derivative of general formula

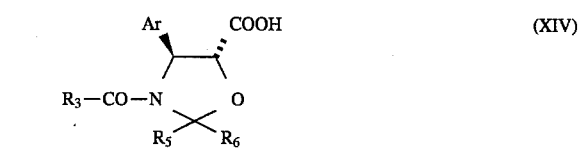

(XIV)

in which Ar and $R_3$ are defined as above and $R_5$ and $R_6$, which are identical or different, represent a hydrogen atom or an alkyl radical containing 1 to 4 carbon atoms or an aryl radical, preferably a phenyl radical optionally substituted by one or more alkoxy radicals containing 1 to 4 carbon atoms, or alternatively $R_5$ represents an alkoxy radical containing 1 to 4 carbon atoms or a trihalomethyl radical such as trichloromethyl and $R_6$ represents a hydrogen atom, or alternatively $R_5$ and $R_6$ together form with the carbon atom to which they are attached a ring having 4 to 7 members, then by esterifying the taxane derivative of general formula (IX) by means of the acid of general formula (XIV) to give a product of general formula:

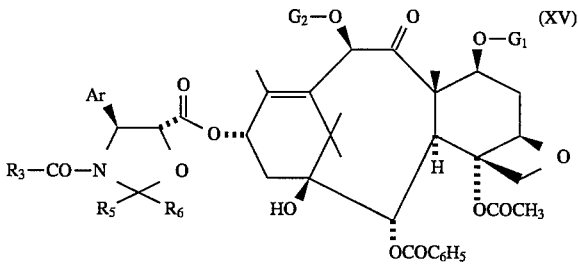

(XV)

in which Ar, $G_1$, $G_2$, $R_3$, $R_5$ and $R_6$ are defined as above, which is converted to the taxane derivative of general formula (VII) by passing, when $R_5$ and $R_6$, which are identical or different, represent an alkyl radical containing 1 to 4 carbon atoms, or an aryl radical, preferably an optionally substituted phenyl radical, or alternatively $R_5$ represents a trihalomethyl radical or a phenyl radical substituted by a trihalomethyl radical and $R_6$ represents a hydrogen atom, or alternatively $R_5$ and $R_6$ form together with the carbon atom to which they are attached a ring having 4 to 7 members, via a taxane derivative of general formula

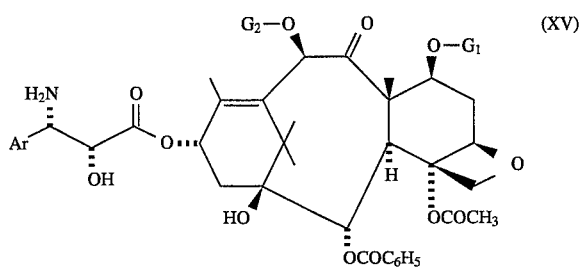

(XV)

which is acylated by means of benzoyl chloride or of a product of general formula (XIII), the procedure being carried out for example under the conditions described in PCT Application WO 9209589, before obtaining a product of general formula:

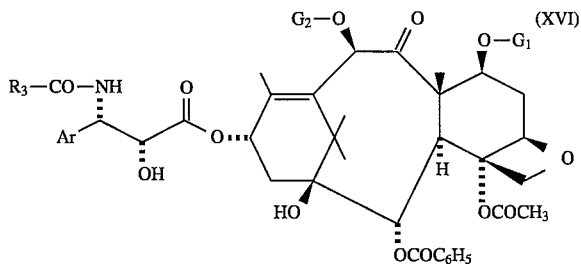

(XVI)

whose protecting groups $G_1$ and $G_2$ are replaced by hydrogen atoms under the conditions described above.

Although the present invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

EXAMPLES

The following non-limiting examples illustrate the invention.

Example 1

To 0.91 g of a 3% dispersion of palladium on activated carbon powder, are added a solution of 1.6 g of methyl (2R, 3S)-2-hydroxy-3-[(S)-1-phenyl]ethylamino-3-phenylpropionate in a mixture of 30 cm³ of methanol and 10 cm³ of acetic acid. The reaction mixture is heated to a temperature of 65° C. for 4 hours, with stirring and at a pressure of 2600 kPa (26 bars) of hydrogen, in a 250-cm³ stainless steel autoclave. The reaction mixture is then cooled to a temperature close to 20° C. and filtered over sintered glass containing celite. The sintered glass is washed with 3 times 10 cm³ of methanol and the filtrates are pooled and then concentrated to dryness under reduced pressure (2.7 kPa) at a temperature close to 40° C. The residue is supplemented with 40 cm³ of distilled water and the solution obtained is alkalinized to a pH close to 7 by addition of 8 cm³ of a 7.5N aqueous solution of sodium hydroxide and then extracted with 4 times 60 cm³ of dichloromethane. The organic phases are pooled, dried over magnesium sulphate, filtered and then concentrated to dryness under reduced pressure (2.7 kPa) at 40° C. 0.74 g of white crystals are thus obtained which are recrystallized from 10 cm³ of a mixture of diisopropyl ether and ethyl acetate (70-30 by volume) to give 0.54 g of methyl (2R, 3S)-3-amino-2-hydroxy-3-phenylpropionate in the form of white crystals with a melting point of 101° C. and whose characteristics are as follows:

specific rotation: $[\alpha]_D^{20}=-19°$ (c=0.51; methanol)

NMR spectrum (300 MHz; $CDCl_3$) δ (ppm): 2.22 (m,3H: —$NH_2$ and OH); 3.81 (s,3H: —$COOCH_3$); 4.32 (s,2H: —CHOH and —$CHNH_2$); 7.20 to 7.5 (m,5H: —$C_6H_5$).

Methyl (2R,3S)-2-hydroxy-3-[(S)-1-phenyl]-ethylamino-3-phenylpropionate may be prepared in the following manner:

A solution of 0.8 g of (3R,4S)-3-hydroxy-4-phenyl-1-[(S)-1-phenyl]ethyl-2-azetidinone in a mixture of 30 cm³ of methanol and 6 cm³ of a 6N aqueous solution of hydrochloric acid is refluxed (65° C.) for 20 hours, then cooled to a temperature close to 20° C. and concentrated to dryness under reduced pressure (2.7 kPa) at a temperature close to 40° C. The residue is supplemented with 20 cm³ of distilled water and alkalinized up to a pH close to 7 by addition of a 7.5N aqueous solution of sodium hydroxide and then extracted with 3 times 25 cm³ of dichloromethane. The organic phases are pooled, dried over magnesium sulphate, filtered and then concentrated to dryness under reduced pressure (2.7 kPa) at 40° C. 0.74 g of methyl (2R, 3S)-2-hydroxy-3-[(S)-1-phenyl]ethylamino-3-phenylpropionate is thus obtained in the form of a pale yellow oil whose characteristics are as follows:

specific rotation: $[\alpha]_D^{20}=-22.7°$ C. (c=1.00; methanol)

NMR spectrum (200 MHz; $CDCl_3$) δ (ppm): 1.34 (d,3H, J=7 Hz: —$CCH_3$); 2.7 (m,2H: —CNHC— and —OH); 3.71 (q,1H,J=7 Hz: —CHNH—); 3.84 (s,3H: —$COOCH_3$); 4.2 (d,1H,J=4 Hz: —CHOH—); 4.35 (d,1H,J =4 Hz: —CHNH—); 7.20 to 7.45 (m,5H: —$C_6H_5$).

(3R,4S)-3-hydroxy-4-phenyl-1-[(S)-1-phenyl]-ethyl-2-azetidone may be prepared according to one of the following methods:

1) To a mixture of 120 cm³ of a 1N aqueous solution of potassium hydroxide and 90 cm³ of tetrahydrofuran, is added over 35 minutes, with stirring and at a temperature close to 0° C., a solution of 3.3 g of a mixture in a 75/25 molar ratio of the two diastereoisomers of 3-acetoxy-4-phenyl-1-[(S)-1-phenyl]ethyl-2-azetidinone, form A and form B, in 120 cm³ of tetrahydrofuran. When the addition is completed, the reaction medium is stirred at a temperature close to 0° C. for 1 hour and then supplemented with 120 cm³ of a saturated aqueous solution of sodium hydrogen carbonate and 100 cm³ of distilled water. The aqueous phase is separated by decantation and reextracted with 3 times 100 cm³ of ethyl acetate. The organic phases are pooled, dried over magnesium sulphate, filtered and then concentrated to dryness under reduced pressure (2.7 kPa) at 40° C. 2.8 g of white crystals are thus obtained which are recrystallized from 35 cm³ of a mixture of ethyl acetate and hexane (80-20 by volume) to give 1.92 g of (3R,4S)-3-hydroxy-4-phenyl-1-[(S)-1-phenyl]ethyl-2-azetidinone in the form of white crystals with a melting point of 162° C. and whose characteristics are as follows:

specific rotation: $[\alpha]_D^{20}=+132°$ C. (c=1.08; methanol)

NMR spectrum (200 MHz; $CDCl_3$) δ (ppm): 1.41 (d,3H, J=7 Hz: —$CHCH_3$); 2.36 (d,1H,J=8.5 Hz: —OH); 4.58 (d,1H,J=4.5 Hz: —$CHC_6H_5$); 4.90 (dd,1H,J=8.5 Hz and 4.5 Hz: —CHOH—); 5.06 (q,1H,J =7 Hz: —$CHCH_3$); 7.20 to 7.50 (m,5H: —$C_6H_5$).

The mixture of the A form and of the B form of 3-acetoxy-4-phenyl-1-[(S)-1-phenyl]ethyl-2-azetidone may be prepared in the following manner:

To a solution of 14.63 g of (S)-N-benzylidene(1-phenyl-ethylamine) in 180 cm³ of chloroform, are added, with stirring and at a temperature close to 20° C., 19.6 cm³ of triethylamine, then the reaction mixture is cooled to a temperature close to −20° C. and 5.17 cm³ of 2-acetoxyacetyl chloride in 90 cm³ of chloroform are added dropwise, over 75 minutes and while this temperature is maintained. The solution maintained is stirred for 16 hours at a temperature close to 20° C. and then supplemented with 300 cm³ of a 2.7N aqueous solution of hydrochloric acid. The organic phase is separated by decantation, washed with twice 300 cm³ of distilled water and then with 300 cm³ of a saturated aqueous solution of sodium hydrogen carbonate, dried over magnesium sulphate, filtered and then concentrated to dryness under reduced pressure (2.7 kPa) at 40° C. 16.5 g of a brown oil are thus obtained which are purified by chromatography on 800 g of silica (0.04–0.063 mm) contained in a column with a diameter of 6.8 cm [eluent: cyclohexane-ethyl acetate (70-30 by volume)], recovering 22 cm³ fractions. Fractions 100 to 153 are pooled and concentrated to dryness under reduced pressure (0.27 kPa) at 40° C. 10.65 g of a mixture in a 75/25 molar ratio of the two diastereoisomers of 3-acetoxy-4-phenyl-1-[(S)-1-phenyl]-ethyl-2-azetidinone are thus obtained in the form of a yellow oil.

(S)-N-benzylidene(1-phenylethylamine) may be prepared according to the method described by M. Furukawa et al., Chem. Pharm. Bull., 1977, 25(1), 181–184.

2) By carrying out the procedure as above, but starting with 100 mg of a mixture in a 70/30 molar ratio of the two diastereoisomeres of 3-isobutyryloxy-4-phenyl-1-[(S)-1-phenyl]ethyl-2-azetidinone, form A and form B, 82 mg of (3R,4S)-3-hydroxy-4-phenyl-1-[(S)-1-phenyl]ethyl-2-azetidinone are obtained in the form of white crystals with a melting point of 162° C. whose physical characteristics are identical to those of the product obtained above.

The mixture of the A and B forms of 3-isobutyryloxy-4-phenyl-1-[(S)-1-phenyl]ethyl-2-azetidinone may be prepared by carrying out the procedure as above but starting with 1.91 g of (S)-N-benzylidene(1-phenylethylamine) and 1 g of 2-isobutyryloxyacetyl chloride. 1.27 g of a mixture in a 70/30 molar ratio of the two diastereoisomers of 3-isobutyryloxy-4-phenyl-1-[(S)-1-phenyl]ethyl-2-azetidinone are obtained in the form of a yellow oil.

2-isobutyryloxyacetyl chloride may be prepared in the following manner:

To a solution of 5 g of glycolic acid in 100 cm³ of dichloromethane, maintained under an argon atmosphere, are added, with stirring and at a temperature close to 20° C., 18.3 cm³ of triethylamine and then the reaction mixture is cooled to a temperature close to 5° C. and 13.8 cm³ of isobutyryl chloride are added dropwise over 30 minutes while this temperature is maintained. The solution obtained is stirred for 3 hours at a temperature close to 20° C. The precipitate which appears is separated by filtration and washed with twice 10 cm³ of dichloromethane. The pooled filtrates are washed with 60 cm³ of a saturated aqueous solution of ammonium chloride, then with 30 cm³ of a saturated aqueous solution of sodium chloride, dried over magnesium sulphate, filtered and then concentrated to dryness under reduced pressure (2.7 kPa) at 40° C. 13 g of a yellow oil are thus obtained to which are added 24 cm³ of sulphinyl chloride. The solution obtained is refluxed for 2.5 hours and then distilled under reduced pressure (0.07 kPa; 0.5 mmHg). 3.4 g of 2-isobutyryloxyacetyl chloride are thus obtained in the form of a colorless liquid which distils off at 45°–50° C., at a pressure of 0.07 kPa.

3) To 43 mg of a 10% dispersion of palladium on carbon powder, are added a solution of 91 mg of a mixture in a 60/40 molar ratio of the two diastereoisomers of 3-benzyloxy-4-phenyl-1-[(S)-1-phenyl]ethyl-2-azetidinone, form A and form B, in 6 cm³ of methanol and then 32 mg of ammonium formate. The reaction mixture is maintained stirring and under an argon atmosphere for 72 hours at a temperature close to 20° C., then 56 mg of a 10% dispersion of palladium and 128 mg of ammonium formate are added. The reaction mixture is maintained stirring at this temperature for 26 hours. The reaction mixture is then filtered on sintered glass containing celite. The sintered glass is washed with 3 times 5 cm³ of dichloromethane and then the pooled filtrates are concentrated under reduced pressure (2.7 kPa) at a temperature close to 40° C. 70 mg of white crystals are thus obtained which are purified by chromatography on silica gel deposited on plates (gel 1 mm thick; 20 times 20 cm plate) in 10 mg fractions. After location under U.V. rays of the zone corresponding to the desired product, this zone is scraped and the silica is recovered and then washed on sintered glass with 10 times 5 cm³ of dichloromethane and with 5 times 2 cm³ of methanol. The filtrates are pooled and concentrated to dryness under reduced pressure (0.27 kPa) at 40° C. 28 mg of (3R, 4S)-3-hydroxy-4-phenyl-1-[(S)-1-phenyl]ethyl-2-azetidinone are thus obtained in the form of white crystals with a melting point of 162° C. whose physical characteristics are identical to those of the product obtained above.

The mixture of the A and B-forms of 3-benzyloxy-4-phenyl -1-[(S)-1-phenyl]ethyl-2-azetidinone may be prepared by carrying out the procedure as above but starting with 2.0 g of (S) -N-benzylidene (1-phenylethylamine) and 1.38 g of 2-benzyloxyacetyl chloride. 1.25 g of a mixture in a 60/40 molar ratio of the two diastereoisomers of 3-benzyloxy-4-phenyl-1-[(S)-1-phenyl]ethyl-2-azetidinone are thus obtained in the form of a yellow oil.

Example 2

To a solution of 0.53 g methyl (2R,3S)-3-amino-2-hydroxy-3-phenylpropionate in 8 cm³ of dichloromethane, maintained under an argon atmosphere, are added 0.25 g of sodium hydrogen carbonate and then, dropwise, at a temperature close to 20° C., a solution of 0.73 g of di-tert-butyl dicarbonate in 2 cm³ of dichloromethane. The solution obtained is stirred for 72 hours at a temperature close to 20° C. and then supplemented with 20 cm³ of distilled water. The aqueous phase is separated by decantation and then reextracted with twice 10 cm³ of dichloromethane. The organic phases are pooled, dried over magnesium sulphate, filtered and then concentrated to dryness under reduced pressure (2.7 kPa) at 40° C.

0.45 g of methyl (2R,3S)-3-tert-butoxy-carbonylamino-2-hydroxy-3-phenylpropionate are thus obtained after crystallization from diisopropyl ether, in the form of white crystals with a melting point of 135° C. whose physical characteristics are identical to those described in European Patent EP 0,414,610:

specific rotation: $[\alpha]_D^{20}$=−2.6° (c =1; methanol) $[\alpha]_D^{20}$= −7.4° (c=1.03; chloroform)

NMR spectrum (200 MHz; CDCl₃) δ (ppm): 1.42 (s, 9H: —NHCOOC(CH₃)₃); 3.16 (d,1H,J=5 Hz: —OH); 3.87 (s,3H: —COOCH₃); 4.48 (m,1H: —CHOH); 5.22 (broad d,1H,J=10.5 Hz: —CHNHCOOC(CH₃)₃); 5.39 (d,1H,J=10.5 Hz: —NHCOOC(CH₃)₃); 7.20 to 7.45 (m, 5H: —C₆H₅).

The product thus obtained may be converted to Taxotere under the conditions described in European Patent EP 0,336,841.

Example 3

To 1 g of a 10% dispersion of palladium on activated carbon powder, is added a solution of 5.05 g of methyl (2R,3S)-2-hydroxy-3-[(S)-1-phenyl]ethylamino-3-(4-fluorophenyl)propionate in a mixture of 95 cm$^3$ of methanol and 32 cm$^3$ of acetic acid. The reaction mixture is heated at a temperature of 65° C. for 5 hours, with stirring and at a pressure of 2300 kPa (23 bars) of hydrogen, in a 1000-cm$^3$ stainless steel autoclave. The reaction mixture is then cooled to a temperature close to 20° C. and filtered on sintered glass containing celite. The sintered glass is washed with 3 times 30 cm$^3$ of methanol and the filtrates are pooled and then concentrated to dryness under reduced pressure (2.7 kPa) at a temperature close to 40° C.

The residue is supplemented with 50 cm$^3$ of distilled water and the solution obtained is alkalinized to a pH close to 7 by addition of a 7.5N aqueous solution of sodium hydroxide and then extracted with 3 times 80 cm$^3$ of dichloromethane. The organic phases are pooled, dried over magnesium sulphate, filtered and then concentrated to dryness under reduced pressure (2.7 kPa) at 40° C. 2.45 g of methyl (2R,3S)-3-amino-2-hydroxy-3-(4-fluoro-phenyl) propionate are thus obtained in the form of cream-colored crystals with a melting point of 105° C. whose physical characteristics are as follows:

NMR spectrum: (300 MHz; CDCl$_3$+є CD$_3$COOD; δ in ppm). 3.56 (s,3H: —COOCH$_3$); 4.61 and 4.69 (2 mt,1H each: —CHOH and —CHNH$_2$); 7.06 [t,J=8.5 Hz, 2H: —C$_6$H$_4$F(—H3 and —H5)]; 7.46 [dd,J=8.5 and 6.5 Hz, 2H: —C$_6$H$_4$F(—H2 and —H6)].

Methyl (2R,3S)-2-hydroxy-3-[(S)-1-phenyl]-ethylamino-3-(4-fluorophenyl)propionate may be prepared in the following manner:

A solution of 5.45 g of (3R,4S)-3-hydroxy-4-(4-fluorophenyl)-1-[(S)-1-phenyl]ethyl-2-azetidinone in a mixture of 175 cm$^3$ of methanol and 35 cm$^3$ of a 6N aqueous solution of hydrochloric acid is refluxed (65° C.) for 18 hours, then cooled to a temperature close to 20° C. and concentrated to dryness under reduced pressure (2.7 kPa) at a temperature close to 40° C. The residue is supplemented with 150 cm$^3$ of distilled water and alkalinized to a pH close to 7 by addition of a 7.5N aqueous solution of sodium hydroxide and then extracted with 3 times 150 cm$^3$ of dichloromethane. The organic phases are pooled, dried over magnesium sulphate, filtered and then concentrated to dryness under reduced pressure (2.7 kPa) at 40° C. 5.08 g of methyl (2R,3S)-2-hydroxy-3-[(S)-1-phenyl]ethylamino-3-(4-fluorophenyl)-propionate are thus obtained in the form of a pale yellow oil whose physical characteristics are as follows:

NMR spectrum: (300 MHz; CDCl$_3$; δ in ppm). 1.26 (d,J=7 Hz, 3H: —CHCH$_3$); 3.60 (q,J=7 Hz, 1H: —CHCH$_3$); 3.79 (s,3H: —COOCH$_3$); 4.12 and 4.19 (2d,J=3 Hz, 1H each: —CHOH and —CHNH—); 7.00 [t,J =8.5 Hz, 2H: —C$_6$H$_4$F(—H3 and —H5)]; 7.10 to 7.40 [mt,7H: —C$_6$H$_5$ and —C$_6$H$_4$F(—H2 and —H6)].

(3R,4S)-3-Hydroxy-4-(4-fluorophenyl) -1-[(S)-1-phenyl]ethyl-2-azetidinone may be prepared in the following manner:

To a mixture of 470 cm$^3$ of a 1N aqueous solution of potassium hydroxide and 250 cm$^3$ of tetrahydrofuran, is added over 75 minutes, with stirring and at a temperature close to 0° C., a solution of 12.4 g of a mixture in a 75/25 molar ratio of the two diastereoisomers of 3-acetoxy-4-(4-fluorophenyl)-1-[(S)-1-phenyl]ethyl-2-azetidinone, form A and form B, in 300 cm$^3$ of tetrahydrofuran. When the addition is completed, the reaction medium is stirred at a temperature close to 0° C. for 2.5 hours and then supplemented with 250 cm$^3$ of a saturated aqueous solution of sodium hydrogen carbonate. The aqueous phase is separated by decantation and rextracted with 3 times 250 cm$^3$ of ethyl acetate. The organic phases are pooled, dried over magnesium sulphate, filtered and then concentrated to dryness under reduced pressure (2.7 kPa) at 40° C.

10.1 g of white crystals are thus obtained which are recrystallised from 55 cm$^3$ of a mixture of ethyl acetate and hexane (80-20 by volume) to give 5.45 g of (3R,4S)-3-hydroxy-4-(4-fluorophenyl)-1-[(S)-1-phenyl]ethyl-2-azetidinone in the form of white crystals with a melting point of 155° C. and whose physical characteristics are as follows:

NMR spectrum: (300 MHz; CDCl$_3$; δ in ppm). 1.29 (d,J=7.5 Hz, 3H: —CHCH$_3$); 3.59 (broad s,1H: —OH); 4.40 (d,J=3.5 Hz, 1H: —CHC$_6$H$_4$F); 4.52 (broad d, J=3.5 Hz, 1H: —CHOH); 4.90 (q,J=7.5 Hz, 1H: —CHCH$_3$); 6.96 [t,J=8.5 Hz, 2H: —C$_6$H$_4$F(—H3 and —H5)]; 7.00 to 7.30 [mt,7H: —C$_6$H$_5$ and —C$_6$H$_4$F(—H2 and —H6)].

The mixture of the A and B forms of 3-acetoxy-4-(4-fluorophenyl)-1-[(S)-1-phenyl]ethyl-2-azetidinone may be prepared in the following manner:

To a solution of 16.8 g of (S)-N-(4-fluoro)benzylidene (1-phenylethylamine) in 220 cm$^3$ of chloroform, are added, with stirring and at a temperature close to 20° C., 20.8 cm$^3$ of triethylamine, then the reaction mixture is cooled to a temperature close to −20° C. and a solution of 8.2 cm$^3$ of 2-acetoxyacetyl chloride in 80 cm$^3$ of chloroform are added dropwise, over 1 hour while this temperature is maintained. The solution obtained is stirred for 16 hours at a temperature close to 20° C. and then supplemented with 200 cm$^3$ of a 2.7N aqueous solution of hydrochloric acid. The organic phase is separated by decantation, washed with twice 200 cm$^3$ of distilled water and then with 200 cm$^3$ of a saturated aqueous solution of sodium hydrogen carbonate, dried over magnesium sulphate, filtered and then concentrated to dryness under reduced pressure (2.7 kPa) at 40° C. 19.7 g of a brown oil are thus obtained which are purified by chromatography on 1100 g of silica (0.04–0.063 mm) contained in a column with a diameter of 8.5 cm [eluent: cyclohexane-ethyl acetate (70-30 by volume)], collecting 60-cm$^3$ fractions. The fractions containing only the desired product are pooled and concentrated to dryness under reduced pressure (0.27 kPa) at 40° C. 13.7 g of a mixture in a 75/25 molar ratio of the two diastereoisomers of 3-acetoxy-4-(4-fluorophenyl)-1-[(S)-1-phenyl]ethyl-2-azetidinone are thus obtained in the form of a yellow oil.

(S)-N-(4-Fluoro)benzylidene(1-phenylethylamine) may be prepared in the following manner:

To a solution of 12.4 g of 4-fluorobenzaldehyde in 80 cm$^3$ of dichloromethane, are added, with stirring and at a temperature close to 20° C., 13 cm$^3$ of (S)-1-phenylethylamine and 6 g of a 4 Å molecular sieve. The reaction mixture is stirred for 16 hours at a temperature close to 20° C. and then filtered on sintered glass containing celite. The sintered glass is washed with three times 20 cm$^3$ of dichloromethane and the filtrates are pooled and then concentrated to dryness under reduced pressure (2.7 kPa) at a temperature close to 40° C. 18.3 g of (S)-N-(4-fluoro)benzylidene(1-phenylethylamine) are thus obtained in the form of an opalescent oil.

Example 4

To a solution of 2.4 g of methyl (2R,3S)-3-amino-2-hydroxy-3-(4-fluorophenyl)propionate in 60 cm$^3$ of dichloromethane, maintained under an argon atmosphere, are added 0.95 g of sodium carbonate and then, dropwise, at a temperature close to 20° C., a solution of 2.46 g of di-tert-butyl dicarbonate in 20 cm³ of dichloromethane. The solution obtained is stirred for 16 hours at a temperature close to 20° C. and then supplemented with 100 cm³ of distilled water. The aqueous phase is separated by decantation and then reextracted with twice 50 cm³ of dichloromethane. The organic phases are pooled, dried over magnesium sulphate, filtered and then concentrated to dryness under reduced pressure (2.7 kPa) at 40° C.

2.35 g of methyl (2R,3S)-3-tert-butoxy -carbonylamino-2-hydroxy-3-(4-fluorophenyl)propionate are thus obtained after recrystallization from diisopropyl ether in the form of white crystals with a melting point of 125° C. which is converted to 4-acetoxy-2α-benzoyloxy-5β,20-epoxy-1β,7β,10β-trihydroxy-9-oxo-11-taxen-13α-yl (2R,3S)-3-tert -butoxycarbonylamino-2-hydroxy-3-(4-fluorophenyl) propionate, the procedure being carried out under the conditions described in European Patent EP 0,336,841.

Example 5

By carrying out the procedure under the conditions described in Example 1, methyl (2R,3S)-3-amino-2-hydroxy-3-(4-trifluoromethylphenyl) propionate is prepared in the form of cream-colored crystals with a melting point of 134° C. by passing via the following intermediates:

methyl (2R,3S)-2-hydroxy-3-[(S)-1-phenyl]ethylamino-3-(4-trifluoromethylphenyl)propionate in the form of a yellow oil, (3R,4S)-3-hydroxy-4-(4-trifluoromethylphenyl)-1-[(S)-1-phenyl]ethyl-2-azetidinone in the form of white crystals with a melting point of 165° C., the mixture of the A and B forms of 3-acetoxy-4-(4-trifluoromethylphenyl)-1-[(S)-1-phenyl]ethyl-2-azetidinone in the form of a white paste, (S)-N-(4-trifluoromethyl)benzylidene(1-phenylethylamine) in the form of white crystals with a melting point below 50° C.

Example 6

By carrying out the procedure as in Example 2, but starting with 2.73 g of methyl (2R,3S)-3-amino-2-hydroxy-3-(4-trifluoromethylphenyl)propionate, 2.43 g of methyl (2R,3S)-3-tert-butoxycarbonylamino-2-hydroxy-3-(4-trifluoromethylphenyl)propionate are obtained in the form of white crystals with a melting point of 120° C. whose physical characteristics are as follows:

NMR spectrum: (300 MHz; DMSO-$d_6$; δ in ppm). 1.40 [s,9H: —NHCOOC(CH$_3$)$_3$]; 3.62 (s,3H: —COOCH$_3$); 4.40 (mt,1H: —CHOH); 5.08 [(dd,J=11 and 4.5 Hz, 1H: —CHNHCOOC(CH$_3$)$_3$]; 5.65 (d,J=6.5 Hz,1H: —OH); 7.40 [d,J=11 Hz,1H: —NHCOOC(CH$_3$)$_3$]; 7.59 and 7.72 (2d, J=8.5 Hz, 2H each: —C$_6$H$_4$CF$_3$(—H3, —H5 and —H2, —H6)].

The product thus obtained is converted to 4-acetoxy-2α-benzoyloxy-5β, 20-epoxy-1β, 7β,10β-trihydroxy-9-oxo-11-taxen-13α-yl (2R,3S)-3-tert-butoxycarbonyl -amino-2-hydroxy-3-(4-trifluoromethylphenyl) propionate, the procedure being carried out under the conditions described in European Patent EP 0,336,841.

Example 7

By carrying out the procedure under the conditions described in Example 1, methyl (2R,3S)-3-amino-2-hydroxy-3-(4-dimethylaminophenyl) propionate is prepared in the form of cream-colored crystals with a melting point of 119° C. by passing via the following intermediates:

methyl (2R,3S)-2-hydroxy-3-[(S)-1-phenyl]ethylamino-3-(4-dimethylaminophenyl)propionate in the form of white crystals with a melting point of 122° C., (3R,4S)-3-hydroxy-4-(4-dimethylaminophenyl)-1-[(S)-1-phenyl]ethyl-2-azetidinone in the form of white crystals with a melting point of 220° C., the mixture of the A and B forms of 3-acetoxy-4-(4-dimethylaminophenyl)-1-[(S)-1-phenyl]ethyl-2 -azetidinone in the form of white crystals with a melting point of 136° C., (S)-N-(4-dimethylamino)benzylidene(1-phenylethylamine) in the form of white crystals with a melting point below 50° C.

Example 8

By carrying out the procedure as in Example 2, but starting with 0.8 g of methyl (2R,3S)-3-amino-2-hydroxy-3-(4-dimethylaminophenyl) propionate, 0.82 g of methyl (2R,3S)-3-tert-butoxycarbonylamino-2-hydroxy-3-(4-dimethylaminophenyl)propionate is obtained in the form of white crystals with a melting point of 120° C. whose physical characteristics are as follows:

NMR spectrum: (200 MHz; DMSO-$d_6$; δ in ppm). 1.39 [s,9H: —NHCOOC(CH$_3$)$_3$]; 2.90 [s, 6H: —N(CH$_3$)$_2$]; 3.59 (s,3H: —COOCH$_3$); 4.21 (dd,J=7.5 and 4.5 Hz, 1H: —CHOH); 4.81 [dd,J=9.5 and 4.5 Hz, 1H: —CHNHCOOC(CH$_3$)$_3$]; 5.47 (d,J=7.5 Hz, 1H: —OH); 7.02 [d,J=9.5 Hz,1H: —NHCOOC(CH$_3$)$_3$]; 6.66 [d,J=8.5 Hz, 2H: —C$_6$H$_4$N(CH$_3$)$_2$(—H3 and —H5)]; 7,12 [2d,J=8.5 Hz,2H: —C$_6$H$_4$N(CH$_3$)$_2$(—H2 and —H6)].

The product thus obtained is converted to 4-acetoxy-2α-benzoyloxy-5β,20-epoxy-1β,7β,10β-trihydroxy -9-oxo-11-taxen-13α-yl (2R,3S)-3-tert-butoxy-carbonylamino-2-hydroxy-3-(4-dimethylaminophenyl)propionate, the procedure being carried out under the conditions described in European Patent EP 0,336,841.

Example 9

To 2.1 g of a 20% dispersion of palladium dihydroxide on activated carbon powder, is added a solution of 5.5 g of methyl (2R,3S)-3-(4-carbamoylphenyl)-2-hydroxy-3-[(S)-1-phenyl]ethylaminopropionate in a mixture of 100 cm³ of methanol and 3 cm³ of acetic acid. The reaction mixture is maintained stirring for 60 hours at a temperature close to 20° C. and at a pressure of 120 kPa (1.2 bars) of hydrogen. The reaction mixture is then filtered on sintered glass containing celite. The sintered glass is washed with 3 times 15 cm³ of methanol and the filtrates are pooled and then concentrated to dryness under reduced pressure (2.7 kPa) at a temperature close to 40° C. The crystals recovered are washed on sintered glass with 20 cm³ of diethyl ether.

4.6 g of methyl (2R,3S)-3-amino-3-(4-carbamoylphenyl)-2-hydroxypropionate are thus obtained in the form of white crystals with a melting point of 206° C. and whose characteristics are as follows:

NMR spectrum: (300 MHz; DMSO-$d_6$; δ in ppm). 1.90 (s,3H: CH$_3$COO—); 3.60 (s,3H: —COOCH$_3$); 4.13 (limiting ab,2H: —CHOH and —CHNH$^+$); 7.30 and 7.95 (2s, 1H each: —CONH$_2$); 7.40 [(d,J=8.5 Hz, 2H:

—C₆H₄CONH₂(—H2 and —H6)]; 7.80 (d,J=8.5 Hz, 2H: —C₆H₄CONH₂(—H3 and —H5)].

Methyl (2R,3S)-3-(4-carbamoylphenyl)-2-hydroxy-3-[(S)-1-phenyl]ethylaminopropionate may be prepared in the following manner:

To a solution of 10 g of (3R,4S)-4-(4-cyanophenyl)-3-hydroxy-1-[(S)-1-phenyl]ethyl-2-azetidinone in 100 cm³ of acetic acid, are added 10.9 g of mercuric acetate. The reaction medium is refluxed for 5 hours, then cooled to a temperature close to 20° C. and concentrated to dryness under reduced pressure (2.7 kPa) at a temperature close to 40° C. The residue is supplemented with 150 cm³ of methanol and concentrated to dryness under reduced pressure (2.7 kPa) at a temperature close to 40° C. 300 cm³ of methanol are added to the residual solid and a gaseous stream of anhydrous hydrochloric acid is injected, with stirring, into the reaction medium, at a temperature close to 40° C. for 1.5 hours. The reaction medium is concentrated to dryness under reduced pressure (2.7 kPa) at 40° C. and then poured into a mixture of 300 cm³ of ethyl acetate, 300 cm³ of distilled water and 100 cm³ of a saturated aqueous solution of sodium hydrogen carbonate. The aqueous phase is separated by decantation and reextracted with twice 250 cm³ of ethyl acetate. The organic phases are pooled, washed with twice 150 cm³ of a 3% aqueous solution of sodium sulphide and then with twice 100 cm³ of distilled water, dried over magnesium sulphate, filtered and then concentrated to dryness under reduced pressure (2.7 kPa) at 40° C. The crystals recovered are washed on sintered glass with 20 cm³ of diethyl ether. 5.5 g of methyl (2R,3S)-3-(4-carbamoylphenyl)-2-hydroxy-3-[(S)-1-phenyl]ethylaminopropionate are thus obtained in the form of white crystals with a melting point of 130° C. whose characteristics are as follows:

NMR spectrum: (300 MHz; CDCl₃; δ in ppm) 1.30 (d,J=7 Hz,3H: —CHCH₃); 3.65 (q,J=7 Hz,1H: —CHCH₃); 3.85 (s,3H: —COOCH₃); 4.25 and 4.35 (2d,J=3.5 Hz,1H each: —CHOH— and —CHNH—); 5.97 and 6.17 (2 unresolved complexes, 1H each: —CONH₂); 7.20 to 7.40 (mt,5H: —C₆H₅); 7.41 [d,J=8.5 Hz, 2H: —C₆H₄CONH₂(H2 and H6)]; 7.81 [d,J=8.5 Hz,2H: —C₆H₄CONH₂(H3 and H5)].

(3R,4S)-4-(4-Cyanophenyl)-3-hydroxy-1-[(S)-1-phenyl]ethyl-2-azetidinone may be prepared in the following manner:

Into a solution of 55.3 g of a mixture in a 65/35 molar ratio of the two diastereoisomers of 3-acetoxy-4-(4-cyanophenyl)-1-[(S)-1-phenyl]ethyl-2-azetidinone, form A and form B, in 550 cm³ of methanol, is injected, with stirring, a gaseous stream of anhydrous ammonia at a temperature close to 0° C. for 3 hours. The reaction medium is concentrated to dryness under reduced pressure (2.7 kPa) at 40° C.

41 g of white crystals are obtained which are recrystallized from a mixture of 280 cm³ of ethyl acetate and 70 cm³ of diethyl ether. The crystals obtained are recrystallized a second time from 160 cm³ of ethyl acetate and then a third time from 100 cm³ of acetonitrile. 10 g of (3R,4S)-4-(4-cyanophenyl)-3-hydroxy-1-[(S)-1-phenyl]ethyl-2-azetidinone are thus obtained in the form of white crystals with a melting point of 139° C. and whose characteristics are as follows:

NMR spectrum: (300 MHz; CDCl₃; δ in ppm) . 1.39 (d,J=7.5 Hz,3H: —CHCH₃); 3.89 (d,J=6.5 Hz, 1H: —OH); 4.54 (d,J=4 Hz,1H: —CHC₆H₅); 4.96 (dd,J= 6.5 and 4 Hz, 1H: —CHC₆H₅); 4.96 (q,J=7.5 Hz, 1H: —CHCH₃); 7.10 to 7.40 (mt,5H: —C₆H₅); 7.43 [d,J= 8.5 Hz, 2H: —C₆H₄CN(—H2 and —H6 )]; 7.66 [d,J= 8.5 Hz,2H: —C₆H₄CN(—H3 and —H5)].

The mixture of the A and B forms of 3-acetoxy-4-(4-cyanophenyl)-1-[(S)-1-phenyl]ethyl-2-azetidinone may be prepared in the following manner:

To a solution of 56.1 g of (S)-N-(4-cyano)benzylidene(1-phenylethylamine) in 600 cm³ of chloroform, are added, with stirring and at a temperature close to 0° C., 47.6 cm³ of triethylamine and then, dropwise, over 3 hours and while this temperature is maintained, a solution of 18.6 cm³ of 2-acetoxyacetyl chloride in 500 cm³ of chloroform. The solution obtained is stirred for 16 hours at a temperature close to 20° C. and then supplemented with 250 cm³ of distilled water. The organic phase is separated by decantation, washed with 250 cm³ of distilled water, dried over magnesium sulphate, filtered and then concentrated to dryness under reduced pressure (2.7 kPa) at 40° C. 76 g of a brown oil are thus obtained which are purified by chromatography on 3500 g of silica (0.04–0.063 mm) contained in a column with a diameter of 15 cm (eluent: dichloromethane). The fractions containing only the desired product are pooled and concentrated to dryness under reduced pressure (0.27 kPa) at 40° C. 55.3 g of a mixture in a 65/35 molar ratio of the two diastereoisomers of 3-acetoxy-4-(4-cyanophenyl)-1-[(S)-1-phenyl]ethyl-2-azetidinone are thus obtained in the form of an opalescent oil.

(S)-N-(4-Cyano)benzylidene(1-phenylethylamine) may be prepared in the following manner:

To a solution of 25 g of 4-cyanobenzaldehyde in 200 cm³ of dichloromethane, are added, with stirring and at a temperature close to 20° C., 24.3 cm³ of (S)-1-phenylethylamine and 12 g of a 4 Å molecular sieve. The reaction medium is stirred for 16 hours at a temperature close to 20° C. and then filtered on sintered glass containing celite. The sintered glass is washed with 3 times 50 cm³ of dichloromethane and the filtrates are pooled and then concentrated to dryness under reduced pressure (2.7 kPa) at a temperature close to 40° C. 41.4 g of (S)-N-(4-cyano)benzylidene(1-phenylethylamine) are thus obtained in the form of a colourless oil.

Example 10

To a solution of 2.2 g of methyl (2R,3S)-3-amino-3-(4-carbamoylphenyl)-2-hydroxypropionate in 50 cm³ of tetrahydrofuran, maintained under an argon atmosphere, are added at a temperature close to 20° C., 1.24 g of sodium hydrogen carbonate and then 1.62 g of di-tert-butyl dicarbonate. The reaction medium is stirred for 48 hours at a temperature close to 20° C. and then concentrated to dryness under reduced pressure (2.7 kPa) at 40° C. and supplemented with 20 cm³ of distilled water. The solid formed is separated by filtration, washed with 10 cm³ of distilled water and then 10 cm³ of diisopropyl ether and air dried.

2.1 g of methyl (2R,3S)-3-tert-butoxycarbonyl-amino-3-(4-carbamoylphenyl)-2-hydroxypropionate are thus obtained in the form of white crystals with a melting point of 232° C. whose physical characteristics are as follows:

NMR spectrum: (300 MHz; DMSO-d₆; δ in ppm). 1.41 [s,9H: —NHCOOC(CH₃)₃]; 3.62 (s,3H: —COOCH₃); 4.38 (d,J=4.5 Hz,1H: —CHOH); 5.02 [dd,J=10 and 4.5 Hz,1H: —CHNHCOOC(CH₃)₃]; 5.65 (broad unresolved complex, 1H: —OH); 7.32 [d,J=10 Hz,1H: —NHCOOC(CH₃)₃]; 7.39 and 8.00 (2s,1H each: —CONH₂); 7.41 [d,J=8.5 Hz,2H: —C₆H₄CONH₂(—H2 and —H6)]; 7.84 [d,J =8.5 Hz,2H: —C₆H₄CONH₂(—H3 and —H5)].

The product thus obtained is converted to 4-acetoxy-2α-benzoyloxy-5β,20-epoxy-1β, 7β,10β-trihydroxy-9-oxo-11-taxen-13α-yl (2R,3S)-3-tert-butoxycarbonylamino-2-hydroxy-3-(4-carbamoylphenyl)propionate, the procedure being carried out under the conditions described in European Patent EP 0,336,841.

Example 11

To a mixture of 1.8 g of methyl (2R,3S)-3-tert-butoxycarbonylamino-3-(4-carbamoylphenyl)-2-hydroxypropionate and 15 cm³ of anhydrous pyridine, maintained under an argon atmosphere, are added, dropwise, at a temperature close to 20° C., 1.97 cm³ of triethylchlorosilane. When the addition is completed, the reaction medium is stirred for 3 hours at a temperature close to 20° C. and then poured into a mixture of 200 cm³ of distilled water and 50 cm³ of dichloromethane. The aqueous phase is separated by decantation and then reextracted with 3 times 50 cm³ of dichloromethane. The organic phases are pooled, dried over magnesium sulphate, filtered and then concentrated to dryness under reduced pressure (2.7 kPa) at 40° C. and the crystals recovered are washed on sintered glass with 20 cm³ of diisopropyl ether.

1.92 g of methyl (2R,3S)-3-tert-butoxycarbonylamino-3-(4-carbamoylphenyl)-2-triethylsilyloxypropionate are thus obtained in the form of white crystals with a melting point of 165° C. whose physical characteristics are as follows:

NMR spectrum: (300 MHz; DMSO-$d_6$; δ in ppm). 0.43 (mt, 6H: —OSi(CH$_2$CH$_3$)$_3$; 0.80 (t,J=7.5 Hz,9H: —OSi(CH$_2$CH$_3$); 1.40 [s,9H —NHCOOC (CH$_3$)$_3$]; 3.56 (s,3H: —COOCH$_3$); 4.42 (d,J=4.5 Hz,1H: —CHOH); 5.04 [dd,J=9.5 and 4.5 Hz,1H: —CHNHCOOC(CH$_3$)$_3$]; 7.33 [d,J=9.5 Hz, 1H: —NH-COOC(CH$_3$)$_3$]; 7.37 and 7.98 (2s,1H each: —CONH$_2$); 7.46 [d,J=8.5 Hz,2H: —C$_6$H$_4$CONH$_2$(—H2 and —H6)]; 7.84 (d,J=8.5 Hz,2H: —C$_6$ H$_4$CONH$_2$(—H3 and —H5)].

To a solution of 1.18 g of methyl (2R,3S)-3-tert-butoxycarbonylamino-3-(4-carbamoylphenyl)-2-triethylsilyloxypropionate in 20 cm³ of anhydrous pyridine, maintained under an argon atmosphere, is added, dropwise, at a temperature close to 0° C., 0.24 cm³ of phosphorus oxychloride. When the addition is completed, the reaction medium is stirred for 3 hours at a temperature close to 0° C. and then poured into a mixture of 100 cm³ of distilled water and 100 cm³ of a saturated aqueous solution of sodium hydrogen carbonate. After stirring for 5 minutes at a temperature close to 20° C., 100 cm³ of dichloromethane are added and then the aqueous phase is separated and it is reextracted with twice 80 cm³ of dichloromethane. The organic phases are pooled, dried over magnesium sulphate, filtered and then concentrated to dryness under reduced pressure (2.7 kPa) at 40° C.

The residual solid is dissolved in 30 cm³ of methanol and supplemented with 3 cm³ of a 1N aqueous solution of hydrochloric acid. The solution obtained is stirred for 45 minutes at a temperature close to 20° C. and then concentrated to dryness under reduced pressure (2.7 kPa) at 40° C. The residual solid is supplemented with 50 cm³ of a saturated aqueous solution of sodium hydrogen carbonate and then extracted with 3 times 30 cm³ of ethyl acetate. The organic phases are pooled, dried over magnesium sulphate, filtered and then concentrated to dryness under reduced pressure (2.7 kPa) at 40° C. The crystals recovered are washed on sintered glass with 20 cm³ of diisopropyl ether.

0.75 g of methyl (2R,3S)-3-tert -butoxycarbonylamino-3-(4-cyanophenyl)-2-hydroxypropionate is thus obtained in the form of white crystals with a melting point of 250° C. whose physical characteristics are as follows:

NMR spectrum: (200 MHz; DMSO-$d_6$; δ in ppm). 1.39 [s,9H: —NHCOOC(CH$_3$)$_3$]; 3.62 (s,3H: —COOCH$_3$); 4.39 (dd,J=8 and 4.5 Hz,1H: —CHOH); 5.05 [dd,J=9.5 and 4.5 Hz,1H: —CHOH); 5.65 (d,J=8 Hz,1H: —OH); 7.40 [d,J=9.5 Hz,1H: —NH-COOC(CH$_3$)$_3$]; 7.53 [d, J=8.5 Hz,2H: —C$_6$H$_4$CN(—H2 and —H6)]; 7.82 (d,J=8.5 Hz, 2H: —C$_6$H$_4$CN(—H3 and —H5)].

The product thus obtained is converted to 4-acetoxy-2α-benzoyloxy-5β,20-epoxy-1β, 7β,10β-trihydroxy-9-oxo-11-taxen-13α-yl (2R,3S)-3-tertbutoxycarbonylamino -2-hydroxy-3-(4-cyanophenyl)propionate, the procedure being carried out under the conditions described in European Patent EP. 0,336,841.

We claim:

1. Process for the preparation of β-phenyl-isoserine and its analogues of formula:

in which Ar represents an aryl radical and R represents a hydrogen atom or an alkyl radical containing 1 to 4 carbon atoms, which is optionally substituted by a phenyl radical, or a phenyl radical, comprising hydrogenolyzing a product of formula:

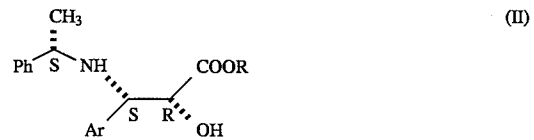

in which Ar and R are defined as above and Ph represents a phenyl radical which is optionally substituted by at least one atom or radical selected from halogen and alkoxy radicals containing 1 to 4 carbon atoms, alkylthio radicals containing 1 to 4 carbon atoms, amino radicals, alkylamino radicals containing 1 to 4 carbon atoms, dialkylamino radicals in which each alkyl portion contains 1 to 4 carbon atoms or nitro radicals.

2. Process according to claim 1, wherein the hydrogenolysis is performed by means of hydrogen in the presence of a catalyst.

3. Process according to claim 2, wherein the catalyst consists of palladium on carbon or palladium dihydroxide on carbon.

4. Process according to claim 2, wherein the procedure is carried out at a hydrogen pressure of between 1 and 50 bars.

5. Process according to claim 2, wherein the procedure is carried out in an organic solvent.

6. Process according to claim 5, wherein the organic solvent is acetic acid optionally combined with an aliphatic alcohol containing 1 to 4 carbon atoms.

7. The product of formula:

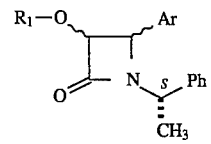

in which Ar represents an aryl radical other than a phenyl radical, Ph represents an optionally substituted phenyl radical and R₁ represents a group which protects the alcohol functional group in the form of an ester or an ether.

8. The product according to claim 7, in which

Ar represents an α- or β-naphthyl radical which is optionally substituted by at least one atom or radical selected from halogen atom and alkyl, aryl, aralkyl, alkoxy, alkylthio, aryloxy, arylthio, hydroxy, hydroxyalkyl, mercapto, formyl, acylamino, aroylamino, alkoxycarbonylamino, amino, alkylamino, dialkylamino, carboxy, alkoxycarbonyl, carbamoyl, dialkylcarbamoyl, cyano, nitro and trifluoromethyl radicals, it being understood that the alkyl radicals and the alkyl portions of the other radicals contain 1 to 4 carbon atoms and that the aryl radical are phenyl or α- or β-naphthyl radicals, Ph represents a phenyl radical which is optionally substituted by at least one atom or radical selected from halogen and alkoxy radicals containing 1 to 4 carbon atoms, alkylthio radical containing 1 to 4 carbon atoms, amino radical, alkylamino radical containing 1 to 4 carbon atoms, dialkylamino radical in which each alkyl portion contains 1 to 4 carbon atoms or nitro radicals and R₁ represents an alkyl, phenylalkyl radical containing more than one carbon atom or phenyl radical or a R'₁—CO radical in which R'₁ represents an alkyl, phenylalkyl or phenyl radical.

9. Product according to claim 8, wherein the halogen atom is fluorine, chlorine, bromine or iodine.

10. Process for the preparation of β-phenylisoserine and its analogues of the formula I

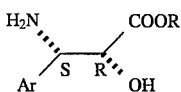

in which

Ar represents an aryl radical and

R represents a hydrogen atom, an alkyl radical containing 1 to 4 carbon atoms, or a phenyl radical, wherein the alkyl radical may be optionally substituted by a phenyl radical, comprising:

a) the cycloaddition of an imine of the formula V

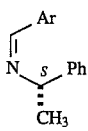

in which

Ar is defined as above and

Ph represents a phenyl radical which is optionally substituted by at least one atom or a radical selected from halogen, alkoxy radicals containing 1 to 4 carbon atoms, alkylthio radicals containing 1 to 4 carbon atoms, amino radicals, alkylamino radicals containing 1 to 4 carbon atoms, dialkylamino radicals in which each alkyl portion contains 1 to 4 carbon atoms, or a nitro radical, onto an acid halide of the formula VI

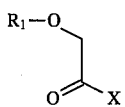

in which

R₁ represents a group protecting the alcohol functional group in the form of an ester or an ether and X represents a halogen atom selected from bromine and chlorine, in the presence of an organic base selected from aliphatic tertiary amines and pyridine, to obtain a product of the formula IV

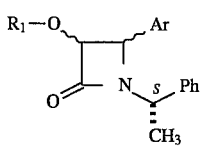

in which Ar, Ph, and R₁ are defined as above;

b) the saponification or hydrogenolysis of the product of formula IV by means of an inorganic base or by the hydrogen optionally generated in situ, in the presence of a catalyst selected from palladium black containing 1 to 10% by weight of palladium, followed by separation of the diastereoisomers obtained to obtain a product of the formula III

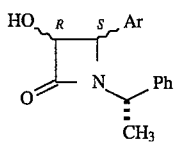

in which Ar and Ph are defined as above;

c) the hydrolysis or alcoholysis of the product of formula III by means of an alcohol in an acidic medium to obtain a product of the formula II

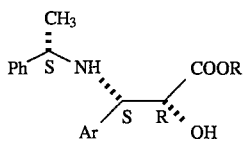

in which Ar, R, and Ph are defined above; and d) hydrolyzing the product of formula II to obtain a product of the formula I

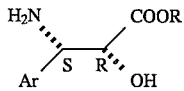

in which Ar and R as defined as above.

* * * * *